United States Patent [19]

Diamantoglou et al.

[11] Patent Number: 5,132,415

[45] Date of Patent: Jul. 21, 1992

[54] METHOD OF MANUFACTURING DEOXYCELLULOSE COMPOUNDS

[75] Inventors: Michael Diamantoglou, Erlenbach; Ernst Kundinger, Breuberg-Neustadt, both of Fed. Rep. of Germany

[73] Assignee: Akzo N.V., Netherlands

[21] Appl. No.: 578,575

[22] Filed: Sep. 7, 1990

[30] Foreign Application Priority Data

Sep. 8, 1989 [DE] Fed. Rep. of Germany ....... 3929883

[51] Int. Cl.$^5$ ...................... C08B 15/00; B01D 13/04; C12N 11/12
[52] U.S. Cl. ........................................ 536/56; 536/124
[58] Field of Search ................................. 536/56, 124

[56] References Cited

U.S. PATENT DOCUMENTS

| | | | |
|---|---|---|---|
| 3,884,631 | 5/1975 | Vigo et al. | 8/194 |
| 3,920,391 | 11/1975 | Vigo et al. | 8/188 |
| 4,981,960 | 1/1991 | Diamantoglou | 536/56 |

FOREIGN PATENT DOCUMENTS

| | | |
|---|---|---|
| 0300250 | of 1988 | European Pat. Off. |
| 2357113 | 12/1982 | Fed. Rep. of Germany |
| 3524596 | 1/1987 | Fed. Rep. of Germany |
| 3840174 | 6/1989 | Fed. Rep. of Germany |
| 3840175 | 6/1989 | Fed. Rep. of Germany |
| 3901945 | 9/1989 | Fed. Rep. of Germany |
| 3901946 | 9/1989 | Fed. Rep. of Germany |
| 3901947 | 9/1989 | Fed. Rep. of Germany |

OTHER PUBLICATIONS

Journal of Applied Polymer Science, vol. 33, 247-282 (1987) No. 2 "Thermal, Morphological and Spectroscopic Studies on Cellulose Modified with Phosphorus, Nitrogen, Sulphur and Halogens" R. Jain.

McCormick et al., "Derivative of Cellulose in Lithium Chloride and N-N-Dimethylacetamide Solutions", Polymer, 1987, vol. 18, Dec., pp. 2317-2323.

Chenoweth et al, "Anaphylatoxin Formation During Hemodialysis: Effects of Different Dialyzer Membranes", Kidney International, vol. 24, 1983, pp. 764-769.

Chenoweth et al., "Biocompatibilityy of Hemodialysis Membranes", Asaio Journal, vol. 7, 1984, pp. 44-49.

Vigo et al., "Recent Advances in the Reaction of Cotton", Textilveredlung 8, No. 3, 1973, pp. 93-97.

"Plastics Find New Roles in Medicine", Chem. Engineering News, 48, 1970, No. 24, pp. 66-67.

Primary Examiner—Nathan M. Nutter
Assistant Examiner—Jeffrey Culpeper Mullis
Attorney, Agent, or Firm—Oliff & Berridge

[57] ABSTRACT

Method of manufacturing deoxycellulose compounds from cellulose in aprotic solvents with LiCl and/or CaCl$_2$, with the solvent, in addition to LiCl or CaCl$_2$, additionally containing bromides, iodides, rhodanides, or dithiocarbamates of the alkaline and/or alkaline earth metals, and the cellulose initially being dissolved in the mixture of aprotic solvent and salts, with a base and/or a basic salt being added at room temperature, and a sulfonic acid halide being added corresponding to the desired degree of substitution, and then being caused to react at temperatures between 16° C. and 100° C.

5 Claims, No Drawings

METHOD OF MANUFACTURING DEOXYCELLULOSE COMPOUNDS

BACKGROUND OF THE INVENTION:

The invention relates to a method of manufacturing deoxycellulose compounds from cellulose in aprotic solvents with LiCl and/or $CaCl_2$.

The Journal *Polymer*, Volume 28, December, 1987, pages 2317-2323, describes the derivatization of cellulose in lithium chloride/N,N-dimethylacetamide solutions by McCormick and Callais. Example 16 describes the preparation of chlorodeoxycellulose with a degree of substitution of 2.3. At best, such a highly substituted product can be processed in a mixture with pure cellulose to form threads or membranes since, after substitution, the properties typical of cellulose membranes and threads are largely lost. On the other hand, however, the reactivity of chlorodeoxycellulose is relatively low in order to utilize the chlorine as a reactive center and gentle operating conditions, for example to immobilize enzymes.

An object of the present invention is to provide a method of preparation of deoxycellulose derivatives characterized by a higher reactivity of the substituents than that of chlorodeoxycellulose.

BRIEF SUMMARY OF THE INVENTION:

In one aspect, the present invention is a method of manufacturing a deoxycellulose compound, comprising:
 i) dissolving cellulose in a mixture of an aprotic solvent, at least one chloride salt, and at least one member selected from the group consisting of bromides, iodides, rhodanides and dithiocarbamate of alkaline or alkaline earth metals;
 ii) subsequently adding an amount of sulfonic acid halide which corresponds to a desired degree of substitution; and
 iii) reacting said mixture at a temperature of from 16° to 100° C.

In a second aspect, the present invention relates to a chloro-substituted deoxycellulose compound which additionally possesses at least one other substituent.

DETAILED DESCRIPTION OF THE PREFERRED EMBODIMENTS:

The object discussed above is achieved by a method characterized by the solvent containing, in addition to LiCl or $CaCl_2$, bromides, iodides, rhodanides, or dithiocarbamate of alkaline and/or alkaline earth metals, with the cellulose initially being dissolved in the mixture of aprotic solvent and salts, adding a base and/or a basic salt at room temperature, and adding a sulfonic acid halide corresponding to the desired degree of substitution, and conducting a reaction at temperatures between 16° C and 100° C.

The method according to the invention makes deoxycellulose compounds accessible which have in addition to a Cl substitution, a residual group substitution with sulfonic acid and partial substitution with bromine, iodine, and/or rhodanide. The ratio of the various substituents can be adjusted first by the ratio of LiCl and/or $CaCl_2$ to the salts with a different by the external reaction conditions. Mixed substitution significantly increases the reactivity of the deoxycellulose compound under gentle reaction conditions.

Preferably N,N-dimethylacetamide (DMAc) and/or N-methylpyrrolidone and/or ethylene urea and/or propylene urea and/or dimethylsulfoxide are used as aprotic solvents.

At temperatures below 15° C for the most part all that occurs is a reaction of cellulose with sulfonic acid halide to form cellulose sulfonic acid ester. The latter reacts above 15° C with the halide or pseudo-halide ions present in the solution to produce mixed substituted cellulose derivatives. Temperatures above 100° C result in sharply decomposed and hence useless cellulose derivatives.

Therefore, the sulfonic acid halide is preferably caused to react at temperatures between 40° C and 70° C.

Under these reaction conditions, the reaction can be controlled very well and the desired degree of substitution can be achieved with good conversion and good selectivity. Preferably, 0.1 to 2 moles per 100 g of cellulose are added to sulfonic acid halide.

A preferred area of application of the deoxycellulose compounds thus produced is the manufacture of reactive cellulosic membranes.

Another preferred application of the deoxycellulose compounds thus formed is the immobilization of enzymes, with the latter applying to molded structures such as threads, films, membranes, and powdered products.

One area of application for the membranes according to the invention is dialyzers, especially for artificial kidneys. In this connection, the biocompatibility of the membranes is of particular importance.

In addition to the fact that dialysis membranes made of synthetic or natural polymers can very easily cause the blood to coagulate when used in artificial kidneys, something which is largely prevented by appropriate drug treatment, a temporary drop in the number of leukocytes often occurs when dialysis membranes made of regenerated cellulose are used when treating a kidney patient with dialyzers that have regenerated-cellulose membranes during the initial stage of dialysis treatment. This effect is known as leukopenia.

Leukopenia is a drop in the number of leukocytes (white blood cells) in the blood stream. The number of white blood cells in man is about 4,000 to 12,000 cells per cc.

Leukopenia during dialysis is most pronounced 15 to 20 minutes after the start of treatment, and the neutrophils (leukocytes which take neutral stains or simultaneously take acidic and basic stains) may disappear almost completely. Then, however, the number of leukocytes recovers within about one hour to nearly the initial value or even exceeds it.

If a new dialyzer is connected after the leukocytes recover, leukopenia occurs once again and to the same degree.

Cellulose membranes cause pronounced leukopenia. Even though the clinical significance of leukopenia has not been scientifically clarified, it is desirable to have a dialysis membrane for hemodialysis that does not exhibit the effect of leukopenia without at the same time having a negative effect on the other highly desirable properties of dialysis membranes made of regenerated cellulose.

In hemodialysis using membranes made from regenerated cellulose, in addition to leukopenia, a pronounced complement activation has also been observed. The complement system within the blood serum is a complex plasma enzyme system consisting of a number of components which serve in different ways to prevent injury caused by the penetration of foreign cells (bacteria, etc.). If antibodies against the invading organism are present, activation can be produced in a complement-specific manner by the complex of antibodies plus the antigen structures of the foreign cells; otherwise, complement activation takes place along an alternative pathway through special surface features of the foreign cells. The complement system is based on a number of plasma proteins. After activation, these proteins react specifically in a certain sequence with one another and eventually a cytotoxic complex is formed which destroys the foreign cell.

Peptides are released from individual components, causing inflammatory phenomena and can sometimes also have undesired pathological consequences for the organism. It is assumed that activation in hemodialysis membranes made of regenerated cellulose takes place via the alternative pathway. These complement activations are determined objectively by determining the complement fragments $C_{3a}$ and $C_{5a}$.

In this connection, we would refer to the following papers: D. E. Chenoweth et al., *Kidney International*, Vol. 24, pages 764 ff, 1983, and D. E. Chenoweth, *Asaio Journal*, Vol. 7, pages 44 ff. 1984.

EXAMPLES

The invention will now be described in greater detail with reference to the examples below. As examples, these specific embodiments of the invention are illustrative only, and are not intended to limit the generic invention disclosed herein.

Complement activation based upon the $C_{5a}$ fragments was evaluated within the scope of the present invention. Heparinized blood plasma (300 ml) was recirculated in vitro over a period of 4 hours with a plasma flow of 100 ml/min through a dialyzer with 1 m² effective exchange area. The $C_{5a}$ fragments in the plasma were determined using the RIA method (Upjohn test). The relative complement activation for the point in time measured was calculated by taking the ratio between the concentration at the time the sample was taken and the initial value in percent. The measured value after 4 hours of recirculation time was used for evaluation. Flat membranes were incubated for 3 hours with heparinized plasma, after which the $C_{5a}$ fragments were determined.

The average degree of polymerization (AP) was determined in a "Cuen" solution according to DIN 54270.

EXAMPLE 1

Using a 1-liter three-necked flask, 48.6 g (0.30 mole) of cellulose (AP =650, measured in "Cuen" solvent) was suspended in 697 g (8 moles) dimethylacetamide and activated at 145° C for 30 minutes under nitrogen. After cooling to 100° C, 64.8 g (1.53 moles) of LiCl and 64.8 g (0.75 mole) of LiBr were added, whereupon the temperature rose 5°–10° C; then the mixture was rapidly cooled to room temperature and stirred overnight. Then 60.6 g (0.60 mole) of triethylamine and 85.7 g (0.45 mole) of toluene sulfonyl chloride were added to the viscous solution in succession. The reaction mixture was kept agitated by stirring for 96 hours at 50° C to complete the reaction. After cooling, the reaction product was precipitated with ethanol, rinsed with water and ethanol, and dried in a vacuum drying cabinet at 50° C. The result was 59 g of a product with the following specifications:

| | | |
|---|---|---|
| Cl content: | 7.80% | DS = 0.47 |
| Br content: | 2.10% | DS = 0.06 |
| S content: | 3.70% | |
| Degree of residual tosylation: | | DS = 0.24 |

A DMAc/LiCl solution containing 7% cellulose derivative was prepared from this derivative and processed into flat membranes. The $C_{5a}$ activation was reduced 86% by comparison with unmodified cellulose membranes.

EXAMPLES 2–6

By methods analogous to Example 1, the deoxycellulose derivatives listed in Table 1 were synthesized by reacting the cellulose dissolved in DMAc/LiCl with toluenesulfonyl chloride in the presence of triethylamine and LiBr, LiI or LiSCN.

TABLE 1

Deoxycellulose Derivatives

| Example | Cl % | Cl DS | Br % | Br DS | J % | J DS | N SCN % | N SCN DS | Residual Degree of Tosylation S % | Residual Degree of Tosylation S DS |
|---|---|---|---|---|---|---|---|---|---|---|
| 2 | 4 | 0.22 | 1.12 | 0.03 | — | — | — | — | 2.8 | 0.17 |
| 3 | 3.1 | 0.16 | 5.5 | 0.13 | — | — | — | — | 1.1 | 0.06 |
| 4 | 3.2 | 0.16 | — | — | 2.5 | 0.04 | — | — | 1.5 | 0.08 |
| 5 | 3.8 | 0.20 | — | — | 4.6 | 0.07 | — | — | 1.3 | 0.08 |
| 6 | 2.3 | 0.12 | — | — | — | — | 2.5 | 0.34 | — | — |

EXAMPLE 7

A. Preparation of Tosyl Cellulose

Using a 2-liter three-necked flask, 48.6 g of Buckeye V68 cellulose (0.3 mole) was suspended in 835.8 g of dimethylacetamide and refluxed for 30 minutes. After the mixture cooled to 100° C, 87.6 g of LiCl was added. With further cooling to room temperature, a clear cellulose solution was obtained within a few hours. Then 73 g of triethylamine (0.72 mole) and an additional 94.4 g dimethylacetamide and 3.7 g LiCl were added and dissolved at room temperature while stirring. Then 114.5 g of p-toluene sulfonyl chloride were dissolved in 188.9 g of dimethylacetamide and added drop by drop for one hour while cooling the reaction mixture in a water bath. The reaction mixture was stirred for another 2.5 hours and then poured into cold water. The precipitated reaction product was washed and dried several times with water and then with ethanol. A total of 87.4 g of a product with the following composition were obtained:

| | | |
|---|---|---|
| C content | 48.4% | |
| H content | 5.0% | |
| Cl content | 0.95% | DS = 0.08 |
| S content | 10.15% | DS = 1.0 |

B. Reacting tosyl cellulose with sodium dithiodiethylcarbamate.

Tosyl cellulose (9.48 g) with DS=1 (0.03 mole) was dissolved in a 0.25 liter three-neck flask in 47.2 g dimethylacetamide. Then 5.13 g of sodium dithiodiethylcarbamate were dissolved in 37.8 g of dimethylacetamide and added to the tosyl cellulose solution. The reaction mixture was stirred for four hours at 60° C and allowed to stand at room temperature for several hours. Then the reaction product was precipitated by pouring it into water, and subsequently rinsed several times with water, ethanol, and finally with diethyl ether. After drying, 68 g of a white, fluffy product with the following composition was obtained:

| | |
|---|---|
| C content | 46.2% |
| H content | 5.9% |
| N content | 3.0% |
| S content | 19.9% |

After spreading a solution of the reaction product in dimethylacetamide and evaporating off the solvent, a flat membrane was obtained.

EXAMPLE 8

A. Preparation of Chlorodeoxycellulose

By a method analogous to Example 7, tosyl cellulose was prepared with an average degree of substitution DS=1. In a 2-liter three-neck flask, 75 g of tosyl cellulose was dissolved in 303 g of dimethylacetamide. Then a solution of 32 g of LiCl in 390 g dimethylacetamide was added to the solution of tosyl cellulose. The reaction mixture was heated to 50° C and agitated at this temperature for 20 hours. The reaction product was precipitated by pouring the solution into water and washed several times with water and ethanol. After drying, 52.8 g of a product with the following composition was obtained.

| | | |
|---|---|---|
| C content | 43.7% | |
| H content | 5.3% | |
| Cl content | 11.25% | DS = 0.61 |
| S content | 4.0% | DS = 0.24 |

B. Reacting Chlorodeoxycellulose with Sodium Dithiodiethylcarbamate

Using a 0.25 l three-neck flask, 6.3 g (0.02 mole) of the above mentioned chlorodeoxycellulose was dissolved in 75.6 g of dimethylacetamide. After adding a solution of 3.4 g sodium dithiodiethylcarbamate (0.02 mole) in 28.3 g dimethylacetamide, the reaction mixture was heated to 60° C and stirred for 8 hours at this temperature. The reaction product was precipitated by pouring the solution into water and washed several times with water and ethanol. After drying, 6.6 g of a light beige powder with the following composition were obtained.

| | |
|---|---|
| C content | 45% |
| H content | 6.2% |
| Cl content | 3.6% |
| N content | 2.7% |
| S content | 14.1% |

After spreading a solution of the reaction product in dimethylacetamide and evaporating off the solvent, a flat membrane was obtained.

EXAMPLES 9 and 10

By methods analogous to Example 8, chlorodeoxycellulose was reacted with various sodium dithiocarbamates. The sodium salts and the composition of the products are shown in Table 2.

TABLE 2

Reaction Products of Chlorodeoxycellulose and Sodium Dithiocarbamate

| Example | Composition of Reaction Products | | | | |
|---|---|---|---|---|---|
| | % C | % H | % Cl | % N | % S |
| 9 Sodium dithiomorpholine carbamate | 42.3 | 5.5 | 14.6 | 2.2 | 12.95 |
| 10 Sodium dithiohydroxyethylpiperazine carbamate | 43.3 | 5.5 | — | 3.8 | 12.85 |

The reaction products can be processed into flat membranes from solution.

We claim:

1. A method of manufacturing a deoxycellulose compound, comprising:
   i) dissolving cellulose in a mixture of an aprotic solvent, at least one chloride salt, and at least one member selected from the group consisting of bromides, iodides, rhodanides and dithiocarbamates of alkaline or alkaline earth metals;
   ii) subsequently adding an amount of sulfonic acid halide greater than zero which corresponds to a desired degree of substitution;
   iii) reacting said mixture at a temperature of from 16° to 100° C.

2. The method of claim 1, wherein said chloride salt is at least one member of the group consisting of LiCl and CaCl$_2$.

3. The method of claim 1 wherein the aprotic solvent is at least one member selected from the group consisting of N,N-dimethylacetamide, N-methylpyrrolidone, ethylene urea, propylene urea, and dimethylsulfoxide.

4. The method of claim 1 wherein said sulfonic acid halide is reacted at temperatures between 40° C. and 70° C.

5. The method of claim 1, wherein 0.1 to 2 moles/100 g of cellulose are added to the sulfonic acid halide.

* * * * *

UNITED STATES PATENT AND TRADEMARK OFFICE
CERTIFICATE OF CORRECTION

PATENT NO. : 5,132,415

DATED : July 21, 1992

INVENTOR(S) : Michael DIAMANTOGLOU et al

It is certified that error appears in the above-identified patent and that said Letters Patent is hereby corrected as shown below:

Col. 1, line 65, after "different" insert --anion and also--.

Signed and Sealed this

Tenth Day of August, 1993

Attest:

MICHAEL K. KIRK

Attesting Officer

Acting Commissioner of Patents and Trademarks